United States Patent
Perez-Abalo et al.

(10) Patent No.: US 9,345,419 B2
(45) Date of Patent: May 24, 2016

(54) METHOD AND APPARATUS FOR THE OBJECTIVE DETECTION OF AUDITIVE DISORDERS

(75) Inventors: Maria Cecilia Perez-Abalo, Ciudad de la Habana (CU); Ernesto Luis Rodriguez-Davila, Ciudad de la Habana (CU); Manuel Sanchez-Castillo, Ciuda de la Habana (CU); Roberto Carlos Sotero-Diaz, Ciuda de la Habana (CU); Alejandro Torres-Fortuny, Ciuda de la Habana (CU); Elsa Santos-Febles, Ciudad de la Habana (CU)

(73) Assignee: CENTRO DE NEUROSCIENCIAS DE CUBA (CU)

( * ) Notice: Subject to any disclaimer, the term of this patent is extended or adjusted under 35 U.S.C. 154(b) by 1226 days.

(21) Appl. No.: 13/055,545

(22) PCT Filed: Jul. 24, 2009

(86) PCT No.: PCT/CU2009/000005
§ 371 (c)(1),
(2), (4) Date: Feb. 16, 2011

(87) PCT Pub. No.: WO2010/009681
PCT Pub. Date: Jan. 28, 2010

(65) Prior Publication Data
US 2011/0144529 A1    Jun. 16, 2011

(30) Foreign Application Priority Data
Jul. 24, 2008   (CU) .................................. 2008-0141

(51) Int. Cl.
*A61B 5/0484*   (2006.01)
*A61B 5/12*   (2006.01)
(52) U.S. Cl.
CPC ............. *A61B 5/04845* (2013.01); *A61B 5/121* (2013.01)

(58) Field of Classification Search
CPC ............................ A61B 5/04845; A61B 5/121
USPC .......................................... 600/544, 545, 559
See application file for complete search history.

(56) References Cited

U.S. PATENT DOCUMENTS 5,954,667 A *   9/1999   Finkenzeller et al. ........ 600/544
6,524,258 B1    2/2003   Sturzebecher et al.
(Continued)

FOREIGN PATENT DOCUMENTS

EP          1444951 A1    8/2004
EP          1611846 A1    1/2006
(Continued)

OTHER PUBLICATIONS

Comparison of Statistical Indicators for the Automatic Detection of 80 Hz Auditory Steady State Responses Jorge Luis Valdes; Maria Cecilia Perez-Abalo et al. Ear and Hearing; Williams & Wilkins 1997; vol. 18(5) Oct. 1997; pp. 420-429.
(Continued)

*Primary Examiner* — Adam J Eiseman
(74) *Attorney, Agent, or Firm* — Marvin Feldman; Lackenbach Siegel, LLP

(57) ABSTRACT

This invention relates to the apparatus for the objective detection of auditive disorders, by recording arising potentials of a steady state with simultaneous acoustic stimulation via the bones or the airway to be used in newborns. The apparatus comprises the necessary means for the independent generation of two different sound stimuli presented to the subject simultaneously via osseous, and airway electroacoustic transducers, the synchronous recording of the cerebral electrical activity of the subject, the continuous evaluation of the contact of the electrodes, the interactive measurement of the levels of ambient noise, and the wireless digital transmission of the bioelectric activity towards a computer.

9 Claims, 3 Drawing Sheets

Block diagram of the apparatus for the recording and stimulation of SSEA

(56) References Cited

U.S. PATENT DOCUMENTS

| | | | |
|---|---|---|---|
| 6,778,955 B2 | 8/2004 | Li et al. | |
| 7,014,613 B2 | 3/2006 | John et al. | |
| 7,197,350 B2* | 3/2007 | Kopke | A61B 5/04845 600/383 |
| 7,370,533 B2* | 5/2008 | Davis | A61B 5/121 381/60 |
| 8,271,075 B2* | 9/2012 | Chuang | A61B 5/0478 600/383 |
| 2006/0073819 A1* | 4/2006 | Lowles | 455/418 |
| 2006/0153396 A1* | 7/2006 | John | 381/60 |
| 2007/0019818 A1* | 1/2007 | Kurz | H04R 25/70 381/60 |
| 2009/0259137 A1* | 10/2009 | Delic et al. | 600/545 |
| 2009/0259140 A1* | 10/2009 | Buchman et al. | 600/559 |

FOREIGN PATENT DOCUMENTS

| | | |
|---|---|---|
| EP | 1854407 A1 | 11/2007 |
| WO | WO 03/099121 A3 | 12/2003 |
| WO | WO 2008/032927 A1 | 3/2008 |

OTHER PUBLICATIONS

A Comparison of Steady-State Evoked Potentials to Modulated Tones in Awake and Sleeping Humans Lawrence T. Cohen, Field W. Rickards; Graeme M. Clark J. Acoust. Soc. Am. 90 (5), Nov. 1991; pp. 2467-2478.

Stimulated Acoustic Emissions from Within the Human Auditory System D.T. Kemp; Auditory Perception Research Lab, et al. J. Acoust. Soc. Am. 64(5) Nov. 1978; pp. 1386-1391.

Auditory Steady-State Responses to Multiple Simultaneous Stimuli Otacio G. Lins; Terence W. Picton 1005 Elsevier Science Ireland Ltd.; Electroencephalography and Clinical Neurophysiology 96 (1995) pp. 420-432.

Human Auditory Evoked Potentials: Possible Brain Stem Components Detected on the Scalp Don L. Jewett; Michael N. Romano; John S. Williston; Department of Physiology and Neurosurgery, University of California Medical Center; San Francisco 94122 Science, vol. 167; Mar. 13, 1970; pp. 1517-1518.

* cited by examiner

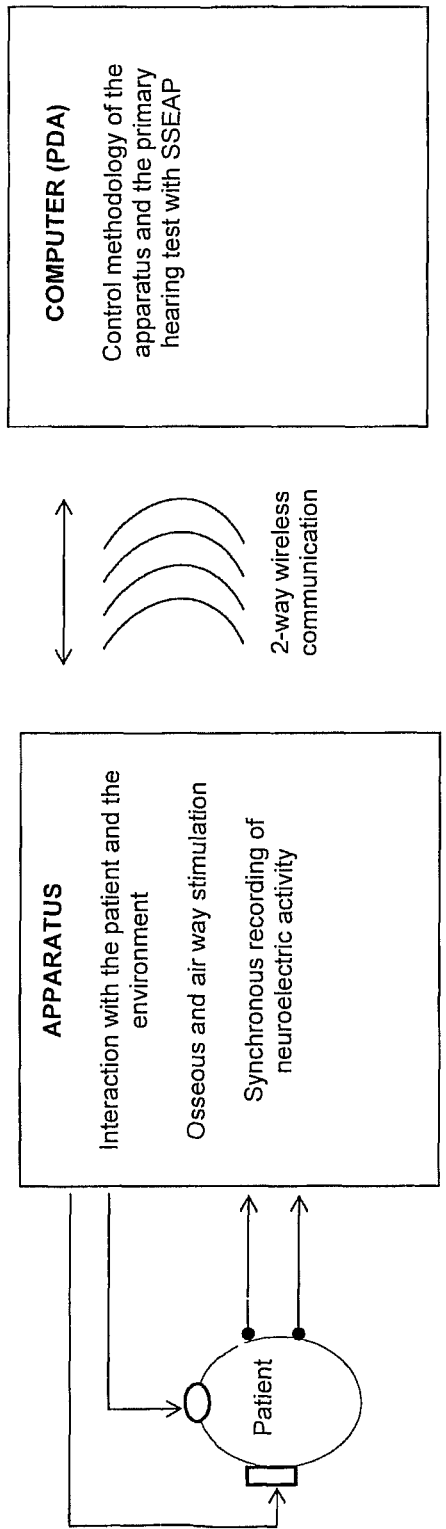
Figure 1. Schematic representation of the system consisting of an apparatus and a personal computer that controls the apparatus

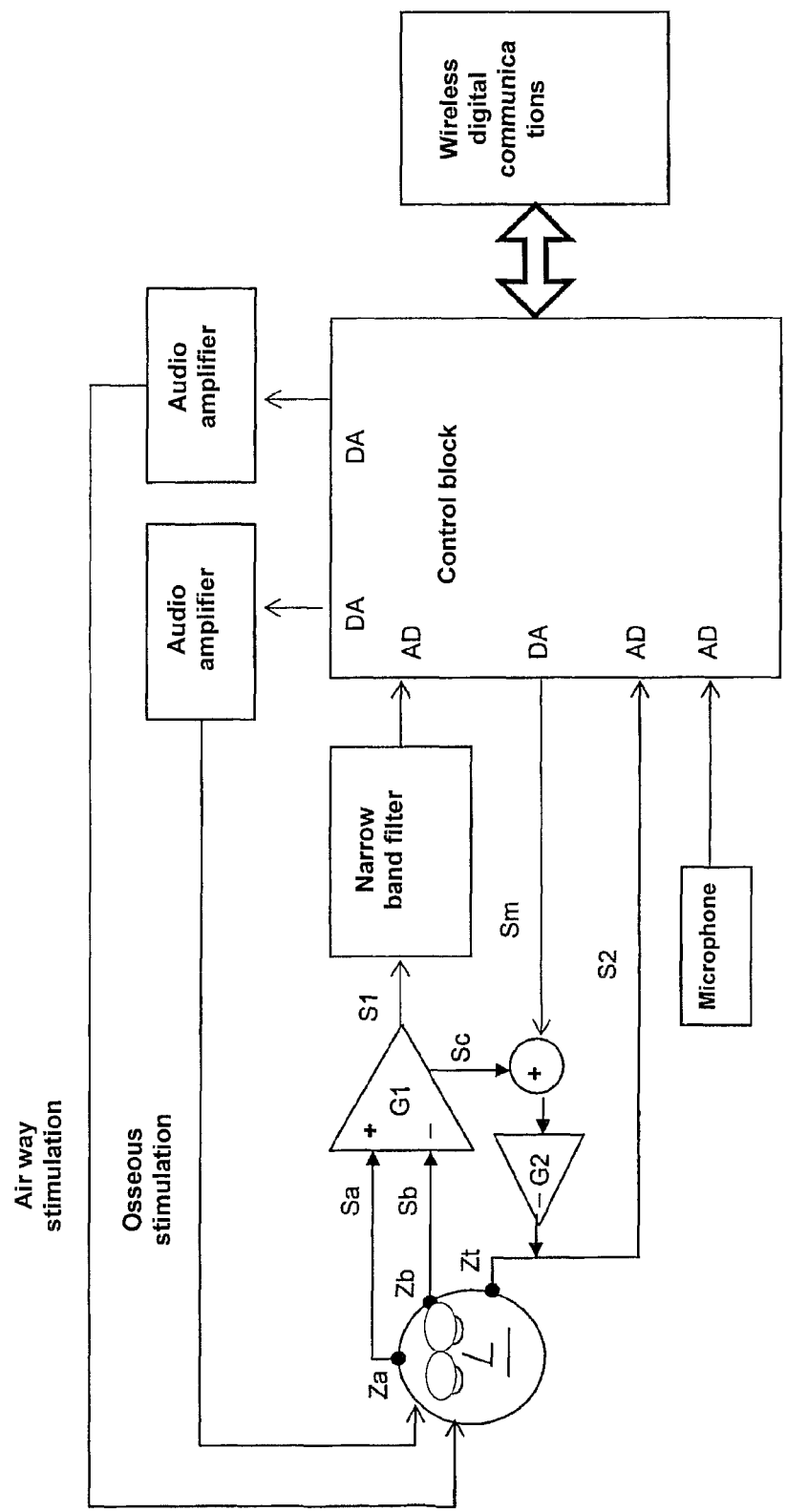
Figure 2. Block diagram of the apparatus for the recording and stimulation of SSEA

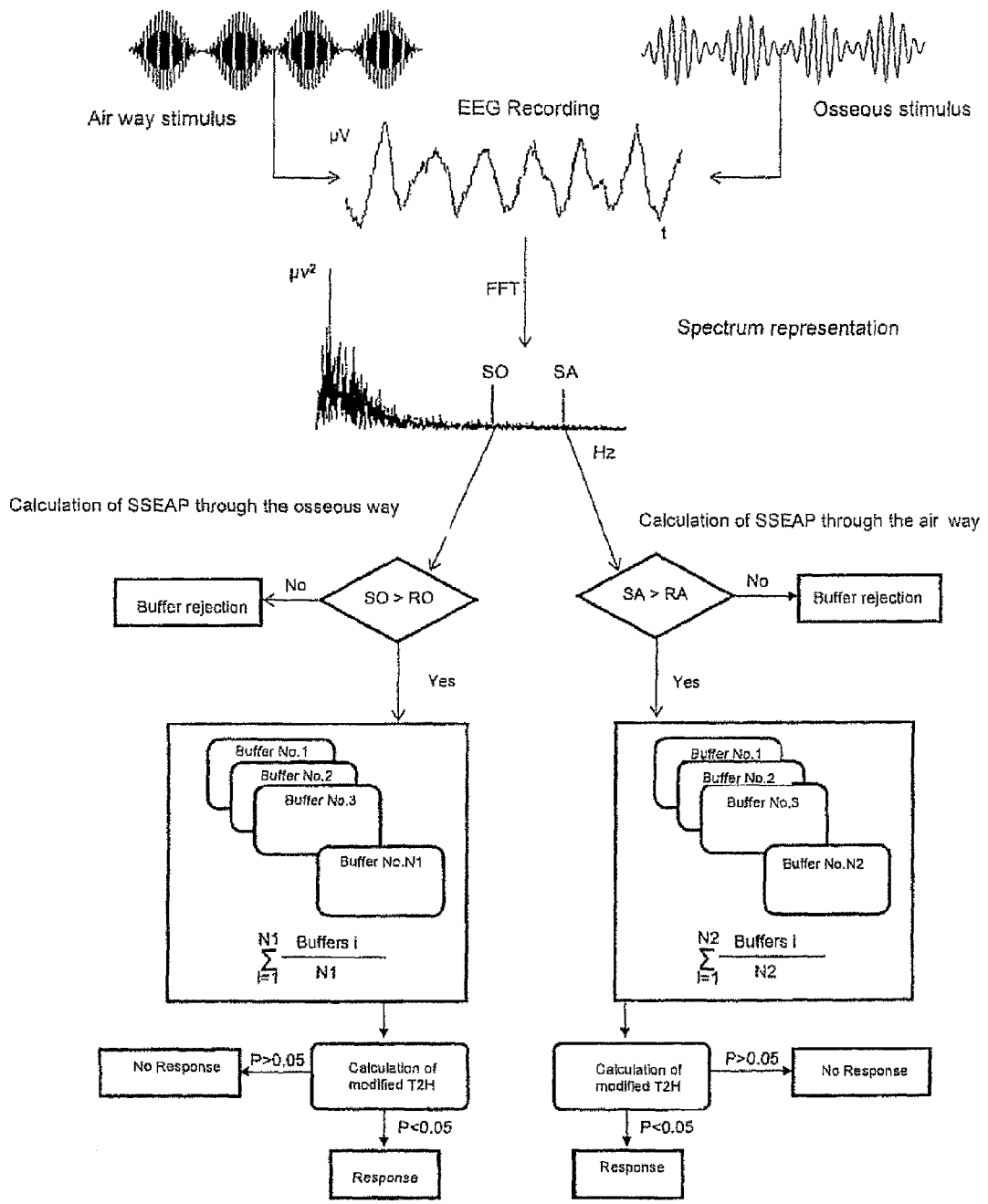
Figure 3. Schematic representation of ASSR by simultaneously air/bone stimulation and selective averaging method according to the residual noise

METHOD AND APPARATUS FOR THE OBJECTIVE DETECTION OF AUDITIVE DISORDERS

PRIOR RELATED APPLICATIONS

This application claims priority to PCT/CU2009/000005, filed Jul. 24, 2009, published as WO2010/009681 on Jan. 28, 2010, and Cuban Patent Application CU 2008-0141, filed Jul. 24, 2008, which applications are incorporated herein in their entireties by reference thereto.

OBJECT OF THE INVENTION

The invention relates to the field of the objective evaluation of hearing by means of brain electrical responses caused by sound stimulation, also known as steady state evoked auditory potentials, to be used with newborn babies, small children and individuals who do not cooperate during a conventional audiometric examination.

BACKGROUND OF THE INVENTION

There is a broad range of commercially available automatically operated portable devices that allow to perform an "objective" assessment of the auditory sensitiveness through the recording and processing of temporary physiological responses caused by short acoustic stimuli. These devices commonly use the Auditory Evoked Potentials of the Brainstem (AEPBT), which are known from Jewett D L, Romano M N, Wilson J S. (Human auditory evoked potentials: Possible brainstem components detected on the scalp. Science 1970; 167:1517-8) and/or oto-acoustic emissions generated at the auditory recipient (OAE), which have been described by Kemp D. (Stimulated acoustic emissions from within the human auditory system. J Acoust Soc Am. 1978; 64:1386-9).

However, these devices and methodologies still have shortcomings that must be solved. A very important problem that still has to be solved is the high rate of "false positives" found during the initial auditory examination of neonates, which is carried out when the neonate stays at the maternity hospital. Many of these neonates (classified as false positives) show temporary hearing losses, caused by problems encountered by the transmission of sound through the structures of the middle ear, and not by a neuronal damage of the recipient (inner ear), which is the main object of the screening tests. Temporary conductive losses in neonates (caused by serum fluid of the middle ear) are spontaneously solved in a few days. However, it is necessary to perform a second test, which generates anxiety among parents, makes the follow-up more complicated, as a result of the large number of cases involved, and has even raised doubts about the implementation of the universal screening programmes.

In order to solve this problem and to make a difference between both types of disorders (conductive and sensorineural losses) it does not suffice to establish the auditory sensitivity vis-á-vis a sound which is presented, in a natural way, through the external acoustic meatus (air conduction mode). In the case of auditory disorders caused by problems in the sound transmission through the outer and middle ear (conductive loss), sound vibrations can be properly perceived if they are directly transmitted to the neural recipient (inner ear) through the bone (bone conduction mode) since, in this case, they do not cross the affected structures of the outer and middle ear. This allows, when evaluating the auditory sensitiveness by means of sounds transmitted through both modes, to discriminate between conductive disorders (where the bone conduction mode yields normal, but air conduction mode does not) and those caused by a permanent damage to the recipient or neural route (where the auditory sensitiveness is also affected, irrespective of the sound transmission route eventually chosen).

The temporary physiological responses to short acoustic stimuli (AEPBT and OAE) show serious limitations in order to assess the bone sensitiveness. It has been acknowledged that the technological process implemented to obtain and identify these responses to the bone conduction mode stimulation is more complicated, requires a great deal of experience on the part of the person in charge of the evaluation, in order to appropriately identify the threshold response, and there are no effective automation procedures, which is unavoidable in the case of a Universal Neonatal Screening.

Steady state auditory potentials (SSEAP), (known from Cohen L T, Richards F M; Clark G M. A comparison of steady state evoked potentials in awake and sleeping humans J. Acousti. Soc. Am. 1991) are a valid alternative for the objective assessment of auditory sensitiveness. These responses consist of constant periodical signals that can be caused by means of long tonal stimuli with amplitude and/or frequency modulation (between 70 and 110 Hz). Considering that these SSEAP are generated at the brainstem, they are not affected by sedation or sleep, which facilitates their use with neonates. As a result of its periodical nature, the SSEAP provoked by modulated tones can be better analysed within the frequency domain (Fourier analysis), and they are represented as spectrum peaks limited to the modulation frequency used. This facilitates their automatic detection through different statistical methods calculated within the domain of frequency (Valdés J. L., Pérez-Abalo M. C, Martin V, Savio G, Sierra C, Rodriguez E, Lins O. "Comparison of Statistical Indicators for the Automatic Detection of 80 Hz Auditory Steady Responses". 18 (1997): 420-429. Sep. 11, 1997). From Lins O G and Picton T W. (Auditory steady-state responses to multiple simultaneous stimuli. Electroencephalogr. Clin. Neurophysiol. 1995; 96: 420-32) it has been also known that multiple SSEAP can be obtained for tonal stimuli that are simultaneously presented, thereby reducing the duration of the hearing test.

As a result of these advantages, several recent patents (U.S. Pat. No. 7,014,613 B2; U.S. Pat. No. 6,778,955 B2; U.S. Pat. No. 6,524,258 B1) propose different alternative methods and apparatuses to facilitate the use of SSEAP for the objective assessment of hearing. Since these responses show a very low amplitude, especially at low ages, and they are disturbed by a higher amount of noise, documents U.S. Pat. No. 7,014,613 B2 and U.S. Pat. No. 6,524,258 B1 claim new types of acoustic stimuli, presented in the air conduction mode to generate responses with a higher amplitude, that can be more easily detected. Document U.S. Pat. No. 7,014,613 B2 also claims a series of methods to render the calculation of the SSEAP more efficient, and proposes to use the weighted averaging method, so that the most noisy records have less weight for the calculation of the multiple SSEAP. However, this method is useful only to reduce the effect of temporary noise contamination (as opposed to the stationary one) and is not appropriate for other sources of noise that re constant along the time (stationary) and that are also present at the SSEAP. On the other hand, the method used to calculate the amplitude of the noise (within the desired range of 70 to 110 Hz) does not allow to accurately ascertain what is happening in the vicinity of each one of the evoked signals or multiple SSEAPs. In this case, the relative weight of a bioelectric record collected, which is adequate for some signals, but not for others, can be proportionally reduced. The patent (U.S. Pat. No. 6,778,955

B2) divulges another method to achieve a more efficient calculation of responses with a low signal-to-noise ratio, which can be applied to temporary responses (OAE) or stable state responses (SSEAP), but also, it only considers those responses that have been generated through sound stimulation presented to the patient by the air way. Therefore, none of these technological and methodological solutions allows to use the multiple SSEAP for a primary hearing test that can discriminate, in a fast and efficient manner, the type of hearing disorder (conductive or sensorineural), if any. In fact, all the automatic hearing screening devices currently existing show the results in a binary format (normal or abnormal audition). Furthermore, no automatic and easy to use SSEAP devices that can be used by a Universal Neonatal Screening Programme are currently commercially available.

DESCRIPTION OF THE INVENTION

The object of this invention is to propose a method and an apparatus, automated and easy to operate, that—through the recording and analysis of steady state evoked auditory potentials—allows to discriminate between the normal and abnormal hearing, identifying, in this latter case, whether the hearing disorder is of a conductive or sensorineural type.

In order to use the multiple SSEAP technique in the Neonatal Screening Programme to discriminate the type of hearing disorder (if any), an apparatus and a method are proposed, integrating the following elements: 1) means to independently generate two different continuous acoustic stimuli and to present them simultaneously to the patient through electro-acoustic bone and air transducers at different intensities; 2) means to measure the ambient noise and, on the basis of the level measured, to regulate the execution of the screening test and the intensity of the air way stimulation; 3) means to evaluate on an on-going basis the contact of the electrodes or sensors used to record the electric activity of the brain; 4) means to control the process used to collect the bioelectric activity of the patient, in a synchronous manner with the generated sound stimuli; 5) means for the wireless digital transfer of the bioelectric activity collected towards a computer. In order to use the apparatus for the purposes of Universal Neonatal Screening, a computer-based methodology is implemented to efficiently detect both responses (bone and air conducted), which improves the signal-to-noise ratio and minimizes the duration of the hearing test, and a procedure for the automated operation that, on the basis of both responses (bone and air conducted) will discriminate between children without hearing disorders and those who show hearing disorders of a conductive or sensorineural type.

Novelty of the Invention

One of the novelties of this invention is the use of the simultaneous stimulation from both the bone and air conduction modes as the basis for a system of stable state evoked auditive potentials, in order to carry out a primary hearing test (screening) among neonates, that may distinguish between a conductive hearing loss and a sensorineural loss (if any). Another novelty, in the context of the design of the method and apparatus herein proposed, is the manner in which the recording conditions are monitored on an on-going basis (ambient noise levels and the contact impedance of the electrodes) to interact with the operator and/or the operation of the apparatus. More precisely, the use of the own active electric circuit of the neutral electrode for the on-going measuring of impedance is an original technological solution for this purpose. Furthermore, the system proposed implements an original method of selective averaging, with an independent assessment of the signal-to-noise ratio and the application of a autoregressive statistical model, known as GARCH (English acronym of "Generalized Autoregressive Conditional Heteroskedasticity") to achieve a more efficient detection of the brain responses, which is an essential aspect, according to the invention. The method used is also original, since, on the basis of the result of the detection of one or another SSEAP response (air conducted and bone way) a conclusion can be reached in connection with the primary test, thus making a difference between normal or abnormal hearing, identifying, in this latter case, the type of disorder and the validity of the result.

Finally, the precise method adopted by the system, consisting of a specific purpose electronic device, which interacts with the patient and establishes a wireless communication with a laptop computer or a PDA device, whose software includes all the necessary methodology to efficiently perform the primary hearing test represents a novel technological solution.

DESCRIPTION OF THE APPARATUS AND METHOD FOR THE OBJECTIVE DETECTION OF AUDITIVE DISORDERS

FIG. 1 shows the system proposed for the objective detection of auditive disorders in newborns, by means of steady state evoked auditive potentials. The system includes a device that comprises the necessary means for the simultaneous stimulation through electro-acoustic transducers for the bone and air conduction modes, and for the synchronous recording of the neuroelectric activity of the patient provoked by such stimuli. The device includes two-way wireless digital communications means to establish a connection with a computer or laptop device (preferably, a personal digital assistant or PDA). The computer is used to perform the control functions of the device, such as the processing of the neuroelectric data, following its own automatic operation method, which is claimed in this invention.

FIG. 2 shows a detailed block diagram of the apparatus. The apparatus includes a control block that allows the digital generation of two different stimuli, and the necessary means to present them to the patient in an independent and simultaneous manner, at different intensities, by means of electro-acoustic transducers for the bone and air conduction modes. The acoustic stimulus used is generated through the following expression:

$$S_t = A\text{-sen}(F_c \cdot t) * (1 + p \cdot \text{sen}(F_M \cdot t))$$

Where:
A: Amplitude of the modulated tone
P: Depth of the modulation
$F_c$: Carrier frequency
$F_M$: Modulating frequency The parameter A is used to weigh the amplitude of the modulated tone.

Preferably, at least a low frequency tone is generated for the bone conduction mode ($\geq 500 < 1000$ Hz) which is amplitude-modulated (100% depth) with a modulation frequency of 90 Hz, while another high frequency tone ($\geq 2000$ Hz$<4000$ Hz) is simultaneously generated for the air way, which it is amplitude-modulated (100% depth) with a modulation frequency of 110 Hz. These stimuli are intensity-weighed according to the electro-acoustic characteristics of each transducer (bone and conduction modes) and presented to the patient at constant (but different) intensities for each way.

The apparatus also includes a channel for the collection of the neuroelectric activity (active element G1 of FIG. 2) which is collected from the patient by means of 2 sensors or recording electrodes, which are placed on specific points of the scalp. This channel implements the necessary means to amplify such neuroelectric activity in a differentiated manner, filtering it within the desired frequency range. As shown in FIG. 2, a third recording electrode (neutral) is connected through a second active element (G2) to attenuate the interference caused by the power distribution network. This same element (G2), which is used to actively control the neutral electrode (or "Patient's ground") is also used to introduce in the patient, through such neutral electrode, a signal generated internally by the apparatus. The object of such signal is to evaluate the contact impedance of the recording electrodes (Za and Zb) and of the neutral electrode (Zt). The output (S1) of the active element G2 is recorded by another signal recording channel of the apparatus, and is used as the basis for the on-going impedance monitoring methodology which is claimed as part of this invention. The apparatus includes a microphone that picks up the ambient noise level, which is recorded by the G3 channel through the active element. Finally, the control block of the apparatus allows the synchronization between the stimuli generation process and the collection of the neuroelectric activity, so that, at each digitized time window or interval corresponding to such neuroelectric activity there is an exact number of cycles of tone stimuli generated, to allow the subsequent detection of the signal or SSEAP. This block also controls the real time, 2-way and wireless transmission between the apparatus and the computer. The method used in this invention guarantees the automatic operation of this apparatus, so that it can be used with neonates to assess the auditory sensitiveness and to early detect eventual disorders, differentiating them from a diagnostic point of view. It consists of the following stages:

1) Positioning in the head of the patient of the recording electrodes and the electro-acoustic transducers for the bone and air conduction stimulation modes;
2) Start-up and self-test of the apparatus;
3) On-going measuring of the impedance of the recording electrodes and the ambient noise levels;
4) Interactive check of the adequate conditions to perform the test, on the basis of the information obtained in the previous stage;
5) Simultaneous bone and air conduction stimulation modes, with synchronous recording of the neuroelectric activity;
6) Transformation of each one of the neuroelectric records obtained in the previous step within the domain of Frequency, by means of a Fourier Analysis;
7) Independent selective averaging for each spectral response or SSEAP by means of an interactive analysis of each record, on the basis of its signal-to-noise ratio;
8) Statistical determination of the presence or the absence of each one of the responses obtained by stimulation in the bone and air conduction modes; and
9) Diagnosis decision about the normal conditions of the auditory sensitiveness or the type of auditive disorder (if any) taken on the basis of the presence of both responses and/or the selective absence of one or another of the responses.

Steps 1 to 5 are performed by the apparatus, and steps 6 to 9 are carried out by programming a proprietary methodology in a general purpose portable computer. This allows to update and/or improve the method used by this invention to detect the responses.

The selective averaging method used in this invention consists of collecting and averaging, on an independent basis for each response or SSEAP, only those neuroelectric records which have an adequate signal-to-noise ratio. One of the peculiarities of this method consists of the fact that, on the basis of the spectrum analysis of each recorded interval, the validity of the record is independently determined for each SSEAP, by comparing the amplitude of the spectrum component of the response (at the relevant modulating frequency) with that of the residual noise measured from N spectrum components found around it. The rejection criterion is based on a value of the signal-to-noise ratio that is lower than one. This is independently performed for each SSEAP (bone and air modes), so that the same neuroelectric record collected might be valid for a signal and rejected for the other one.

In order to improve the signal-to-noise ratio of the SSEAP, a method is used to model the noise present at the artifact-free averaged neuroelectric records, based on a autoregressive statistical model, AR/GARCH.

In this case, the response is modelled in the average of the N artifact-free segments, using the formula:

$$y_t c + \sum_{i=1}^{R} \phi_i y_{t-i} + \varepsilon_t \qquad (0.1)$$

Where $y_t$ is the signal, c is the average, $\phi_i$ are the autoregressive coefficients $\phi_i$, c and $\epsilon_t$ the innovations. The variance of the innovations is:

$$E_{t-1}(\epsilon_t^2) = \sigma_t^2 \qquad (0.2)$$

And we consider that it follows a GARCH process:

$$\sigma_t^2 \kappa + \sum_{i=1}^{P} G_i \sigma_{t-i}^2 + \sum_{j=1}^{Q} A_j \varepsilon_{t-j}^2 \qquad (0.3)$$

Then, we can calculate the parameters of the model (0.1 0.2 0.3), using the maximum plausibility method.

The following step of the method consists of detecting the signal. Once the coefficients of the model have been calculated, we can separate the autoregressive process from the GARCH process that is responsible for the background noise. This way, if we calculate the spectrum of the autoregressive process only, we will obtain a spectrum which is free from background noise, which simplifies that identification of the signal. The spectrum is calculated as:

$$f(v) = \frac{1}{\left|1 - \sum_j \phi_j e^{-2\pi i j v}\right|} \qquad (0.4)$$

Where v represents the frequencies.

In the last step, we use the Hotelling's T2 stadigraph (T2H) whose degrees of freedom have been modified according to the number of spectrum components used for the calculation, in order to determine whether the spectrum component at the modulation frequency of the stimulus (SSEAP) is significantly different from the adjacent spectrum components (noise corresponding to that signal), and therefore, to determine the presence or absence of response.

FIG. 3 shows a schematic representation of the Auditory Steady-State Response (ASSR) by simultaneous air/bone stimulation and selective averaging method according to the residual noise.

Finally, the following criteria are used by the method of this invention to complete the hearing test and reach the final conclusions: 1) if both signals (bone and air modes) reach a stable statistical significance (after n successive calculations)

by means of a Hotelling's T2 stadigraph, it can be concluded that the auditory sensitiveness is normal; 2) If the response found through the bone conduction mode is significant, and in the absence of the air way response, it can be concluded that the disorder or hearing loss is of a conductive type, 3) in the absence of both responses, it can be concluded that the hearing loss is of a sensorineural type, and 4) in the absence of a bone conducted response and in the presence of an air response, the result is doubtful, and the test should be repeated.

The invention claimed is:

1. An apparatus for the objective evaluation of hearing through brain responses or steady state auditive potentials, comprising:

means for simultaneously providing a patient with different stimuli through electro-acoustic transducers for both air and bone conduction modes;

means for synchronous recording of the neuroelectric activity of the patient, further comprising first and second audio channels, said stimuli comprise a first stimulus comprising one or several mixed low frequencies, amplitude modulated, carrier tones with a M1 modulation frequency through the bone transducer and first audio channel, and the second stimulus comprises one or several mixed high frequencies, amplitude modulated, carrier tones with a M2 modulation frequency through the airway transducer and second audio channel, with synchronous recording of the neuroelectric activity caused by the simultaneous bone and airway stimulation;
and
means for processing and analyzing the neuroelectric activity to obtain a result of the primary hearing test for classifying, the hearing disorder as a conductive or sensorineural disorder.

2. The apparatus according to claim 1, further comprising means for collecting and measuring the ambient noise level.

3. The apparatus of claim 2, further comprising means for evaluating the ambient noise value and the impedance values for determining whether a pre-established rejection criterion is met for interruption of the hearing evaluation.

4. An apparatus for objectively evaluating the hearing of a subject comprising:

(a) a first electro-acoustical transducer comprising means for generating a first stimuli comprising first frequencies specific for bone stimulation and providing a resultant first impedance value;

(b) a second electro-acoustical transducer comprising means for generating a second stimuli comprising second frequencies specific for airway stimulation providing a resultant second impedance value, said first frequencies being lower than said second frequencies;

(c) said (a) and (b) further comprise means for continuously and simultaneously stimulating of the respective bone and airway; and (d) means for calculating the respective impedance values of (a) and (b) with the simultaneous stimulation to determine whether there is a conductive or sensorineural disorder in the subject.

5. The apparatus of claim 4, further comprising means for measuring the ambient noise level, wherein the ambient noise level and impedance value are calculated according to a pre-established rejection criterion as to whether or not to interrupt the evaluation of the hearing of the subject.

6. The apparatus of claim 4, said first transducer comprises a bone conductor and said second transducer comprises an airway conductor, and further comprising means for synchronous recording of the neuroelectric activity from the respective bone and airway conductors.

7. The apparatus of claim 5, said first transducer comprises a bone conductor and said second transducer comprises an airway conductor, and further comprising means for synchronous recording of the neuroelectric activity from the respective bone and airway conductors.

8. The apparatus of claim 4, each said electro acoustical transducer comprises a scalp recording electrode.

9. The apparatus claim, 8 further comprising means for measuring the ambient noise level, wherein the ambient noise level and impedance value are calculated according to a pre-established rejection criterion as to whether or not to interrupt the evaluation of the hearing of the subject.

* * * * *